(12) United States Patent
Eggen et al.

(10) Patent No.: US 6,864,357 B2
(45) Date of Patent: Mar. 8, 2005

(54) PROCESS FOR THE PREPARATION OF PEPTIDES

(75) Inventors: Ivo Franci Eggen, Oss (NL); Paulus Bernardus Wilhelmus Ten Kortenaar, Oss (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/199,785

(22) Filed: Jul. 19, 2002

(65) Prior Publication Data

US 2003/0018163 A1 Jan. 23, 2003

(30) Foreign Application Priority Data

Jul. 19, 2001 (EP) .............................................. 01202751

(51) Int. Cl.$^7$ ................................................. C07K 1/00
(52) U.S. Cl. ...................... 530/333; 530/334; 530/338; 530/344; 530/345
(58) Field of Search ................................ 530/333, 334, 530/338, 344, 345

(56) References Cited

U.S. PATENT DOCUMENTS

| | | | | |
|---|---|---|---|---|
| 5,101,059 A | * | 3/1992 | Carpino et al. | ............. 549/388 |
| 5,221,754 A | * | 6/1993 | Carpino et al. | ............... 549/53 |
| 5,510,491 A | * | 4/1996 | Carpino et al. | ............. 546/344 |
| 5,516,639 A | * | 5/1996 | Tindall et al. | ............... 435/7.4 |
| 5,652,336 A | * | 7/1997 | Fife et al. | .................... 530/342 |
| 6,121,488 A | * | 9/2000 | Nikam | ......................... 564/64 |
| 6,204,361 B1 | * | 3/2001 | Carpino et al. | ............. 530/334 |
| 6,277,958 B1 | * | 8/2001 | Aimoto | ....................... 530/334 |
| 6,310,180 B1 | * | 10/2001 | Tam | ............................ 530/339 |
| 6,506,701 B1 | * | 1/2003 | Bolton et al. | .................. 502/20 |
| 2001/0025025 A1 | * | 9/2001 | Viskov | ............................ 514/9 |
| 2002/0127219 A1 | * | 9/2002 | Okkels et al. | ............ 424/94.61 |
| 2003/0017991 A1 | * | 1/2003 | Yan et al. | ...................... 514/18 |

FOREIGN PATENT DOCUMENTS

WO 00 71569 11/2000

OTHER PUBLICATIONS

Ludt, Robert E. (Journal of Organic Chemistry 38(9), 1668–74, 1973).*

Tsuboi, Sadao (Chemistry Letters (9), 1541–2, 1984).*

Dragovich, Peter S. (Journal of Organic Chemistry 62(22), 7872–7876, 1997).*

Mallet, M. (Tetrahedron 38(20), 3035–42, 1982).*

Balamraju, Yuvaraju (Tetrahedron 54(26), 7357–7366, 1998).*

Kazmaier, Uli (Chemical Communications (Cambridge) (22), 2535_2536, 1998).*

Gaylo L M et al: "Ion–Exchange Resins for Solution Phase Parallel Synthesis of Chemical Libraries"; Tetrahedron Letters, Elsevier Science Publishers, Amsterdam, NL; vol. 38, No. 4, Jan. 27, 1997, pp. 513–516.

Suto M J et al: "Solution–Phase Parallel Synthesis Using Ion–Exchange Resins" Tetrahedron, Elsevier Science Publishers, Amsterdam, NL, vol. 54, No. 16, Apr. 16, 1998, pp. 4141–4150.

Mehta A et al: "Improved efficiency and selectivity in peptide synthesis use of triethylsilane as a carbocation scavenger in deprotection of tert butyl esters and tert butoxy-carbonyl–protected sites", Tetrahedron Letters, vol. 33, No. 37, 1992, pp. 5441–5444.

Pinilla et al: Gene (1993) Vo. 128, pp. 71–76.

Kisfaludy et al: Tetrahedron Lett. (1974) vol. 19, pp. 1785–1786.

Mutter, Manfred and Bayer, Ernest: "The Liquid–Phase Method for Peptide Synthesis"; The Peptides, vol. 2, pp. 285–332, 1979.

* cited by examiner

Primary Examiner—Jon Weber
Assistant Examiner—David Lukton
(74) Attorney, Agent, or Firm—William P. Ramey, III

(57) ABSTRACT

The present invention relates to a process for the preparation of peptides using an excess of an activated carboxylic component to acylate an amino component, wherein after the acylation an amine comprising a free anion or a latent anion is used as a scavenger of residual activated carboxylic functions. This process is useful for the preparation of oligo- and polypeptides and, more generally, in the preparation of compounds containing one or more amide bonds.

14 Claims, No Drawings

PROCESS FOR THE PREPARATION OF PEPTIDES

This application claims priority to European Patent application number 01202751.2, filed Jul. 19, 2001.

FIELD OF THE INVENTION

The invention relates to a new and versatile process for the preparation of compounds containing one or more amide bonds, in particular peptides, especially for processes performed in solution.

BACKGROUND OF THE INVENTION

Peptides are synthesized either in solution or on a solid support. In both approaches coupling and deprotection steps repetitively alternate and may be separated by intermittent purifications. An excess of an activated carboxylic component is preferably used in each coupling step to ensure quantitative coupling to an amino component; thus the occurrence of deletion sequences in the final product can be avoided. In solid phase peptide synthesis residual activated carboxylic component is usually removed by filtration at the end of each coupling step. In solution phase synthesis it is usually assumed that the residual activated carboxylic component is destroyed and removed during the intermittent aqueous work-up. Insertion peptide sequences, however, are often encountered in solution phase synthesis as impurities of the final peptide due to incomplete removal of residual (activated) carboxylic component after a coupling step, which subsequently has coupled following deprotection. In order to avoid the occurrence of said side-reactions a scavenging step may be introduced directly after the coupling step to scavenge (inactivate) the residual activated carboxylic functions. Amines are usually applied as scavengers. The use of polyamines as scavengers leads to scavenged compounds which may be actively extracted into a—preferably acidic—aqueous phase, depending on their polarity [e.g. Kisfaludy, L. et al. (1974) *Tetrahedron Lett.* 19, 1785–1786]. This extraction is usually performed before the deprotection step to avoid loss of the growing peptide into the aqueous phase. However, this procedure has in numerous cases been found to result in incomplete intermittent purification due to the hydrophobicity of the scavenged compound: the intrinsic hydrophobicity of the amino acyl part of the carboxylic component is enhanced by the still present amino-protecting group. Aqueous extraction is thus not completely effective.

Recently, Carpino, L. A. et al. [(1999) *J. Org. Chem.* 64, 4324–4338] reported an improvement of the scavenging method. In addition to the use of a polyamine as a scavenger the amino-protecting group 1,1-dioxobenzo[b]thiophene-2-ylmethoxycarbonyl (Bsmoc) was applied in the process. The Bsmoc function has very high lability towards base. As a result thereof, residual activated carboxylic functions are scavenged and Bsmoc functions are removed in one and the same step using a polyamine.

SUMMARY OF THE INVENTION

A new process has now been found for the preparation of peptides, wherein an excess of an activated carboxylic component is used to acylate an amino component, and wherein after the acylation an amine comprising a free anion or a latent anion (i.e. anion forming upon deprotection) is used as a scavenger of residual activated carboxylic functions. This new process allows an essentially arbitrary choice of the protecting group at the N-terminus of the activated carboxylic component, since—in contrast to the Carpino process—deprotection thereof does not necessarily take place under the same reaction conditions as the scavenging of excess of activated carboxylic functions. Furthermore, the process of this invention allows for highly efficient removal of residual activated carboxylic component without encountering the hydrophobicity problems of other prior art processes in which polyamines are used as scavengers. Preferably, the process of the invention takes place in solution. However, the process may also be applied in solid phase peptide synthesis. The process of the invention is also suitable for the preparation of other compounds containing one or more amide bonds.

DETAILED DESCRIPTION

In a preferred embodiment, an amine comprising a latent anion is used as the scavenger. Preferably, the latent anion in the scavenging amine bears a temporary protecting group which can be selectively removed in the presence of any permanent protecting group attached to the growing peptide. In a particularly preferred embodiment the protecting group of the latent anion in the scavenging amine displays a lability similar to that of the temporary protecting group present at the N-terminus of the growing peptide. This allows the deprotection of the scavenger yielding the anion and the N-terminal deprotection of the growing peptide to take place in a single process step. Especially preferred is the process of the invention wherein the temporary protecting groups, present at the N-terminus of the growing peptide and optionally present in the scavenger, are hydrogenolytically removable groups whereas the permanent protecting groups are acidolytically removable protecting groups. Preferably, said temporary protecting groups are of the benzyl type, e.g. (substituted) benzyl and benzyloxycarbonyl groups. A preferred scavenger is a primary amine comprising a free anion or a latent anion, and in particular a C-terminally protected amino acid derivative. Besides carboxylate, the scavenging amine may comprise other anionic functions such as—but not limited to—sulfonate, sulfate, phosphonate, phosphate or phenolate. A highly preferred amino acid for use as a scavenger is β-alanine or a derivative thereof (e.g. an ester or silyl ester derivative). The most preferred scavenger is benzyl β-alaninate or a salt thereof.

A thiol comprising a free or a latent anion may also be used as a scavenger instead of an amine comprising a free or a latent anion according to the process of this invention.

The scavenger is preferably used in a two- to sixfold molar excess with respect to the residual active component that needs to be scavenged.

The use of a scavenger according to the present invention leads to hydrophilic scavenged compounds which may be actively extracted into a basic aqueous phase after the deprotection step: upon deprotection (if applicable), hydrophilicity is enhanced by the presence of both a free amino function and a free carboxylic function in the scavenged species. Thus, the process of this invention results in a very effective intermittent purification due to the possibility of actively extracting a hydrophilic scavenged compound. In addition, a possibly present excess of carboxylic component which was not activated and whose temporary protecting group was also removed during deprotection, is extracted from the reaction mixture at the same time.

The new process of this invention may conveniently be used in the preparation of oligo- and polypeptides and, more generally, in the preparation of compounds containing one or more amide bonds.

A suitable process according to the present invention is the coupling of an excess of a carboxylic component to an amino component, wherein the carboxylic function is preactivated or activated in situ using a coupling reagent and, if desired, an additive. Following the coupling step, residual activated carboxylic functions are scavenged by adding the scavenger to the reaction mixture. Subsequently, temporary protecting groups are removed using suitable methods known in the art, followed by removal of the scavenged compound by basic aqueous extraction. At the same time, a possibly present excess of carboxylic component which was not activated and whose temporary protecting group was also removed during deprotection, is extracted from the reaction mixture.

The term amino component refers to a molecule comprising a free amino function. In particular, the amino component may be any amine, amino acid or oligopeptide which bears a free amino function and whose other functional groups are protected in such a manner that they do not interfere with the desired coupling reaction. The C-terminal function of the applied amino acid or oligopeptide may be protected as a substituted or unsubstituted amide or as an ester; examples of the latter include—but are not limited to—methyl, ethyl, t-butyl, benzyl, phenacyl, 3-(3-methyl) pentyl (Mpe), 2-(2-phenyl)propyl (Pp), 2-chlorotrityl (Clt), diphenyl(4-pyridyl)methyl (PyBzh), dicyclopropylmethyl (Dcpm), 9-fluorenylmethyl (Fm), allyl (All), 2-(trimethylsilyl)ethyl (Tmse), 4-{N-[1-(4,4-dimethyl-2,6-dioxocyclohexylidene)-3-methylbutyl]-amino}benzyl (Dmab) esters and enzymatically cleavable esters [Roeske, R. W. (1981) in: 'The Peptides', vol. 3 (Gross, E. and Meienhofer, J., eds.) Academic Press, New York, pp. 101–136; for Mpe: Karlström, A. and Undén, A. (1996) Tetrahedron Lett. 37, 4343–4246; for Pp: Yue, C. et al. (1993) Tetrahedron Lett. 34, 323–326; for Clt: Athanassopoulos, P. et al. (1995) Tetrahedron Lett. 36, 5645–5648; for PyBzh: Mergler, M. et al. (2001) P154, $2^{nd}$ International Peptide Symposium & $17^{th}$ American Peptide Symposium; for Dcpm: Carpino, L. A. et al., (1995) J. Org. Chem. 60, 7718–7719; for Fm: Al-Obeidi, F. et al. (1990) Int. J. Peptide Protein Res. 35, 215–218; for All: Kunz, H. et al. (1985) Int. J. Peptide Protein Res. 26, 493–497; for Tmse: Sieber, P. (1977) Helv. Chim. Acta 60, 2711–2716; for Dmab: Chan, W. C. et al. (1995) J. Chem. Soc., Chem. Commun., 2209–2210]. Functions of the t-butyl type or functions of similar lability are preferred for the permanent protection of other functional groups in the amino component; these include—but are not limited to—t-butyl ($^{t}$Bu) for the protection of the Asp, Glu, Ser, Thr and Tyr side chains, t-butoxycarbonyl (Boc) for the protection of the Lys and Trp side chains, trityl (Tit) for the protection of the Asn, Gln and His side chains and 2,2,5,7,8-pentamethylchromane-6-sulfonyl (Pmc) or 2,2,4,6,7-pentamethyldihydrobenzofurane-5-sulfonyl (Pbf) for the protection of the Arg side chain [Barany, G. and Merrifield, R. B. (1980) in: 'The Peptides', vol. 2 (Gross, E. and Meienhofer, J., eds.) Academic Press, New York, pp. 1–284; for Trp(Boc): Franzén, H. et al. (1984) J. Chem. Soc., Chem. Commun., 1699–1700; for Asn(Trt) and Gln(Tit): Sieber, P. and Riniker, B. (1991) Tetrahedron Lett. 32, 739–742; for His(Trt): Sieber, P. and Riniker, B. (1987) Tetrahedron Lett. 28, 6031–6034; for Pmc: Ramage, R. and Green, J. (1987) Tetrahedron Lett. 28, 2287–2290; for Pbf: Carpino, L. A. et al. (1993) Tetrahedron Lett. 34, 7829–7832].

The term carboxylic component refers to a molecule comprising a free carboxylic function. In particular, the carboxylic component may be any carboxylic acid, amino acid or oligopeptide which bears a free carboxylic function and whose other functional groups are protected in such a manner that they do not interfere with the desired coupling reaction. In a preferred embodiment, the amino group of the applied amino acid or oligopeptide is temporarily protected by a benzyloxycarbonyl (Z) function; other examples include—but are not limited to—the Boc, Trt, fluoren-9-ylmethoxycarbonyl (Fmoc), 2-(methylsulfonyl) ethoxycarbonyl (Msc), allyloxycarbonyl (Alloc) functions, functions of the arylsulfonyl type, such as ortho-nitrobenzenesulfonyl (o-NBS) and enzymatically cleavable functions [Geiger, R. and König, W. (1981) in: 'The Peptides', vol. 3 (Gross, E. and Meienhofer, J., eds.) Academic Press, New York, pp. 1–99; for Alloc: Kunz, H. and Unverzagt, C. (1984) Angew. Chem. 96, 426–427; for arylsulfonyl: Fukuyama, T. et al. (1997) Tetrahedron Lett. 38, 5831–5834]. Functions of the t-butyl type or functions of similar lability are preferred for the permanent protection of other functional groups in the carboxylic component as described above for the amino component. The carboxylic component may be preactivated as an active ester, preferably an N-hydroxysuccinimide, benzotriazol-1-yl, pentafluorophenyl or 4-nitrophenyl ester, a halide, an N-carboxyanhydride or as a symmetric anhydride. Alternatively, the carboxylic component may be activated in situ as a mixed anhydride or using a coupling reagent, such as a carbodiimide, preferably N,N'-dicyclohexylcarbodiimide (DCC) or 1-(3'-dimethylaminopropyl)-3-ethylcarbodiimide hydrochloride (EDC), a uronium or a phosphonium salt in the possible presence of a coupling additive, preferably N-hydroxysuccinimide (HONSu), 1-hydroxybenzotriazole (HOBt), 3-hydroxy-4-oxo-3,4-dihydro-1,2,3-benzotriazine (HOOBt), 1-hydroxy-7-azabenzotriazole (HOAt) or 6-chloro-1-hydroxybenzotriazole (Cl-HOBt) and if required in the presence of a tertiary amine ['The Peptides', vol. 1 (1979) (Gross, E. and Meienhofer, J., eds.) Academic Press, New York; Li, P. and Xu, J.-C. (2000) Chin. J. Chem. 18, 456–466].

The temporary protecting group may be removed according to methods known in the art (vide supra). The Z function may be removed by hydrogenolysis using (standard) procedures that apply, e.g. hydrogen gas or formate as a hydrogen donor. During this process all benzyl-type protecting groups are removed and protecting groups of the t-butyl type or functions of similar lability are maintained. The latter may be removed by acidolysis according to the methods known in the art.

A person skilled in the art will understand what is meant with the term basic aqueous extraction. However, basic aqueous extractions are preferably performed using aqueous solutions of sodium hydrogencarbonate or sodium carbonate, if desired in the presence of sodium chloride or potassium nitrate. The term active aqueous extraction refers to an extraction in which either an amino component is extracted under acidic conditions in the protonated form (ammonium) or a carboxylic component is extracted under basic conditions in the deprotonated form (carboxylate).

The invention is further illustrated by the following examples, which are not to be interpreted as a limitation of this invention.

EXAMPLE 1
H—Asp(O$^t$Bu)—Phe—O$^t$Bu

To a stirred suspension of 5.52 g of H—Phe—O$^t$Bu.HCl in a mixture of ethyl acetate and dichloromethane at 20° C., were added 7.76 g of Z—Asp(O$^t$Bu)—OH, 3.24 g of 1-hydroxybenzotriazole, 4.20 g of 1-(3'-dimethylaminopropyl)-3-ethylcarbodiimide hydrochloride and 4.62 ml of 4-methylmorpholine. After stirring the resulting solution until completion of the reaction, 1.21 ml of 4-methylmorpholine and 3.51 g of benzyl β-alaninate p-toluenesulfonate salt were added. The mixture was stirred for another 30 minutes and was extracted with 5% $Na_2CO_3$/10% NaCl, 5% $KHSO_4$/10% NaCl and 5% $Na_2CO_3$/10% NaCl.

The organic layer containing the protected dipeptide Z—Asp(O$^t$Bu)—Phe—O$^t$Bu was subjected to catalytic hydrogenolysis in the presence of palladium on charcoal. Upon completion of the reaction, 5% $Na_2CO_3$/10% NaCl was added and the resulting suspension was filtered. The residue was washed with a mixture of ethyl acetate and dichloromethane, and the combined organic filtrates were extracted with 5% $Na_2CO_3$/10% NaCl, 30% NaCl and water. The organic layer was evaporated to dryness to give the desired dipeptide in quantitative yield. Purity: 98.4% by reversed phase HPLC (24 to 68% acetonitrile in 0.1% trifluoroacetic acid in 29 minutes at 220 nm, 2.0 ml/min, 5 micron $C_{18}$ column). Identity: m/z 393.4[M+H]$^+$ by electrospray MS; $^1$H NMR (CDCl$_3$) δ 1.41 (s, 9H), 1.46 (s, 9H), 1.63 (bs, 2H), 2.39 (dd, 1H) 2.79 (dd, 1H), 3.39 (d, 2H), 3.65 (m, 1H), 4.72 (m, 1H), 7.17–7.32 (m, 5H), 7.81 (d, 1H).

EXAMPLE 2
H—Leu—Phe—NH—(CH$_2$)$_7$—CH$_3$

To a stirred solution of 2.12 ml of n-octylamine in ethyl acetate at 20° C., were added 4.61 g of Z—Phe—OH, 2.08 g of 1-hydroxybenzotriazole, 2.71 g of 1-(3'-dimethylaminopropyl)-3-ethylcarbodiimide hydrochloride and 1.55 ml of 4-methylmorpholine. After stirring the resulting suspension until completion of the reaction, 0.78 ml of 4-methylmorpholine and 2.26 g of benzyl β-alaninate p-toluenesulfonate salt were added. The mixture was stirred for another 30 minutes and was extracted with 5% $Na_2CO_3$/10% NaCl, 5% $KHSO_4$/10% NaCl and 5% $Na_2CO_3$/10% NaCl.

The organic layer containing Z—Phe—NH—(CH$_2$)$_7$—CH$_3$ was diluted with 1-methyl-2-pyrrolidinone and subjected to catalytic hydrogenolysis in the presence of palladium on charcoal. Upon completion of the reaction, 30% NaCl was added and the resulting suspension was filtered. The residue was washed with ethyl acetate, and the combined organic filtrates were extracted with 5% $Na_2CO_3$/10% NaCl and 30% NaCl.

To the organic layer containing H—Phe—NH—(CH$_2$)$_7$—CH$_3$ at 20° C., were added 4.09 g of Z—Leu—OH, 2.08 g of 1-hydroxybenzotriazole, 2.71 g of 1-(3'-dimethylaminopropyl)-3-ethylcarbodiimide hydrochloride, 1.55 ml of 4-methylmorpholine and 1-methyl-2-pyrrolidinone. After stirring the resulting suspension until completion of the reaction, 0.78 ml of 4-methylmorpholine and 2.26 g of benzyl β-alaninate p-toluenesulfonate salt were added. The mixture was stirred for another 30 minutes and was extracted with 30% NaCl, 5% $Na_2CO_3$/10% NaCl, 5% $KHSO_4$/10% NaCl and 5% $Na_2CO_3$/10% NaCl.

The organic layer containing Z-Leu-Phe-NH-(CH$_2$)$_7$-CH$_3$ was diluted with 1-methyl-2-pyrrolidinone and subjected to catalytic hydrogenolysis in the presence of palladium on charcoal. Upon completion of the reaction, 5% $Na_2CO_3$/10% NaCl was added and the resulting suspension was filtered at 45° C. The residue was washed with ethyl acetate, and the combined organic filtrates were extracted with 5% $Na_2CO_3$/10% NaCl, 30% NaCl and water. The organic layer was evaporated to dryness to give the desired product in 85% yield.

Purity: 99.3% by reversed phase HPLC (24 to 68% acetonitrile in 0.1% trifluoroacetic acid in 29 minutes at 220 nm, 2.0 ml/min, 5 micron $C_{18}$ column). Identity: m/z 390.4 [M+H]$^+$, 412.4 [M+Na]$^+$, 388.2 [M−H]$^−$, 434.2 [M+HCOO]$^−$ by electrospray MS; $^1$H NMR (CDCl$_3$) δ 0.89 (m 9H), 1.12–1.39 (m, 14H), 1.50–1.60 (m, 3H), 3.01–3.22 (m, 4H), 3.35 (dd, 1H), 4.53 (dd, 1H), 5.90 (t, 1H), 7.19–7.32 (m, 5H), 7.83 (d, 1H).

CONCLUSION

The purity and identification of the obtained products demonstrate that the excesses of (activated) carboxylic component have been removed completely and no insertion peptide sequences have been formed using the process of this invention.

What is claimed is:

1. A process for the preparation of a compound containing one or more amide bonds using an excess of activated carboxylic component to acylate an amino component, wherein after completion of the acylation reaction an amine comprising a latent anion is added as a scavenger of the residual activated carboxylic functions, which latent anion bears a temporary protecting group which can be selectively removed, followed by a deprotection step resulting in hydrophilic scavenged compounds which may be actively extracted into a basic aqueous phase.

2. The process of claim 1 wherein the temporary protecting group is selectively removed in the presence of a permanent protecting group.

3. The process of claim 1 wherein the compound being prepared is a peptide.

4. The process of claim 2 where the permanent protecting group is attached to the compound.

5. The process of claim 1 wherein the latent anion in the scavenging amine bears a temporary protecting group which displays a lability similar to that of the temporary protecting group present at the N-terminus of the growing compound.

6. The process of claim 1 herein the temporary protecting group is a hydrogenolytically removable groups.

7. The process of claim 2 wherein the permanent protecting group is an acidolytically removable group.

8. The process of claim 6 wherein the temporary protecting group is of the benzyl type.

9. The process of claim 1 wherein the scavenger is a primary amine.

10. The process of claim 9 wherein the primary amine is a C-terminally protected amino acid derivative.

11. The process of claim 10 wherein the amino acid is β-alanine or a derivative thereof.

12. The process of claim 1 wherein the scavenger is a benzyl β-alaninate or a salt thereof.

13. The process of claim 1 comprising performing the process in solution.

14. The process of claim 1 further comprising an aqueous extraction step.

* * * * *